(12) United States Patent
Jeong

(10) Patent No.: US 8,801,731 B2
(45) Date of Patent: Aug. 12, 2014

(54) TOOL FOR MINIMALLY INVASIVE SURGERY

(76) Inventor: Chang Wook Jeong, Seoul (KR)

( * ) Notice: Subject to any disclaimer, the term of this patent is extended or adjusted under 35 U.S.C. 154(b) by 245 days.

(21) Appl. No.: 12/995,302

(22) PCT Filed: May 28, 2009

(86) PCT No.: PCT/KR2009/002833
§ 371 (c)(1),
(2), (4) Date: Nov. 30, 2010

(87) PCT Pub. No.: WO2009/145572
PCT Pub. Date: Dec. 3, 2009

(65) Prior Publication Data
US 2011/0106146 A1  May 5, 2011

(30) Foreign Application Priority Data

May 30, 2008  (KR) .................. 10-2008-0051248

(51) Int. Cl.
*A61B 19/00*  (2006.01)
(52) U.S. Cl.
USPC ........... 606/130; 475/7; 475/9; 74/68; 74/483
(58) Field of Classification Search
CPC ...... A61B 17/29; A61B 19/22; A61B 17/003; A61B 2017/2927; A61B 2019/2238; A61B 2017/291
USPC ........... 606/205–209, 1, 124; 74/10, 10.8, 98, 74/89.13, 505, 490.01, 640, 68, 105, 483; 600/104, 141–142; 475/7, 9, 10
See application file for complete search history.

(56) References Cited

U.S. PATENT DOCUMENTS 5,828,813 A * 10/1998 Ohm ............................ 700/260
6,394,998 B1 * 5/2002 Wallace et al. ................... 606/1
(Continued)

FOREIGN PATENT DOCUMENTS

| EP | 1886633 A2 | 2/2008 |
|---|---|---|
| JP | 2008036219 A | 2/2008 |
| KR | 1020070079038 A | 8/2007 |

OTHER PUBLICATIONS

International Search Report for PCT Application PCT/KR2009/002833, Korean Intellectual Property Office, Dec. 30, 2009.

*Primary Examiner* — Gary Jackson
*Assistant Examiner* — Sidharth Kapoor

(57) ABSTRACT

The present invention relates to an easy-to-control tool for minimally invasive surgery. In accordance with an aspect of the present invention, there is provided a tool for minimally invasive surgery comprising, an elongated shaft having a predetermined length, an adjustment handle manually controllable by a user, a pitch direction handling part and a yaw direction handling part positioned around one end of the elongated shaft for transferring motions in pitch and yaw directions following the actuation of the adjustment handle, a pitch direction actuating part and a yaw direction actuating part positioned around the other end of the elongated shaft for operating corresponding to the operations from the pitch direction handling part and the yaw direction handling part, respectively, an end effector controllable by the pitch direction actuating part and the yaw direction actuating part, and a plurality of cables for transferring the from the pitch direction handling part and the yaw direction handling part to the pitch direction actuating part and the yaw direction actuating part, respectively.

20 Claims, 13 Drawing Sheets

(56) References Cited

U.S. PATENT DOCUMENTS

| | | |
|---|---|---|
| 7,642,895 B2 * | 1/2010 | Fitzgibbon et al. .......... 340/5.53 |
| 2003/0036748 A1 * | 2/2003 | Cooper et al. .................... 606/1 |
| 2004/0167515 A1 * | 8/2004 | Petersen et al. ................. 606/49 |
| 2004/0199147 A1 * | 10/2004 | Nishizawa et al. ............... 606/1 |
| 2006/0074415 A1 * | 4/2006 | Scott et al. ...................... 606/45 |
| 2006/0155262 A1 * | 7/2006 | Kishi et al. ........................ 606/1 |
| 2007/0179476 A1 | 8/2007 | Shelton et al. |
| 2007/0208375 A1 * | 9/2007 | Nishizawa et al. ........... 606/205 |

* cited by examiner

TOOL FOR MINIMALLY INVASIVE SURGERY

PRIORITY

The present application claims priority under 35 U.S.C. §371 to PCT Application PCT/KR2009/002833, filed on May 28, 2009, which claims priority to Korean Patent Application No. 10-2008-0051248, filed on May 30, 2008, the disclosures of which are hereby incorporated by reference in their entireties.

FIELD OF THE INVENTION

The present invention relates to an easy-to-control tool for minimally invasive surgery, and more specifically, to a tool, which includes an adjustment handle connected to one end of a predetermined shaft and an end effector that is connected to the other end of the shaft and controllable merely through the actuation of the adjustment handle, so as to perform minimally invasive surgery.

BACKGROUND OF THE INVENTION

Minimally invasive surgery is a surgical approach that involves use of instruments inserted through several tiny incision openings to perform a surgery causing minimal tissue trauma.

This minimally invasive surgery relatively reduces changes in metabolism of the patient in the period of post-surgical care, so it is beneficial to rapid recovery of the patient. Therefore, using such minimally invasive surgery shortens length of a hospital stay of the patient after the surgery and allows patients to return to normal physical activities more quickly. In addition, minimally invasive surgery causes less pain and reduces scar to patients after surgery.

The most general form of the minimally invasive surgery is endoscopy. Among them, a laparoscopy that involves minimally-invasive inspection and operation inside abdominal cavity is known as the most general form of endoscopy. To operate the standard laparoscopic surgery, an abdomen of the patient is insufflated with gas, and small incisions (about ½ inch or less) are formed for use as an entrance of a tool for the laparoscopic surgery, through which a trocar is inserted. In general, laparoscopic surgical tools include a laparoscope (for observation of a surgical site) and other working tools. Here, the working tools are similar in structure to the conventional tools used for small incision surgery, except that the end effector or working end of each tool is separated from its handle by an elongated shaft. For instance, working tools may include a clamp, a grasper, scissors, a stapler, needle holder, and so forth. To perform the surgery, a user, such as a surgeon, puts the working tool into a surgical site through the trocar, and manipulates it from the outside of abdominal cavity. Then, the surgeon monitors the procedure of the surgery through a monitor that displays the image of the surgical site that is taken by the laparoscope. The endoscopic approach similar to this is broadly used in retroperitoneoscopy, pelviscopy, arthroscopy, cisternoscopy, sinuscopy, hysteroscopy, nephroscopy, cystoscopy, urethroscopy, pyeloscopy, and so on.

Although this minimally invasive surgery has a number of advantages, it has shortcomings in the difficulty of approaching the conventional minimally invasive surgical tools to a surgical site and the inconvenient or complicate manipulation of such tools because of an end effector connected to a rigid and long shaft. Particularly, since the traditional end effector has no bending portion like a joint, it is difficult to perform a dexterous handling required for surgery. These shortcomings are the main impediment to the wide expansion of minimally invasive surgery.

To overcome these shortcomings of the traditional minimally invasive surgery, recently, a robotic assisted platform called the da Vinci® surgical system has been developed by Intuitive Surgical, Inc. The robotic assisted surgical system currently being commercialized mainly uses a master-slave type robot, which is constituted by an operating console where an operator performs an operation, a robotic cart where a robot performs an operation, and an endoscopic stack being connected thereto. An endoscopic stack in the robotic surgical system has a joint that can move in a pitch direction and a yaw direction, and thus can transfer hand motions of the operator almost exactly. Also, the robotic surgical system has a function of tremor reduction or a function of motion scaling to differentiate robot motion from hand motion in terms of scale, and can secure a three dimensional vision.

However, this robotic surgical system is very expensive equipment, and moreover, it costs a tremendous amount of money to install and maintain after installation. This equipment is also bulky and very heavy (even the robotic cart alone is about 2 m tall and as heavy as 544 kg). Needless to say, it is difficult to move the equipment around, so the surgery has to be performed only in a place where the system is already installed. Besides, in case of using the robotic system, surgeons feel lack of tactile sense, as compared with using the traditional tools for laparoscopic surgery.

SUMMARY OF THE INVENTION

The present invention is directed to solve all of the problems mentioned above.

It is, therefore, an object of the present invention to provide a tool for minimally invasive surgery with an end effector that operates in correspondence to motions in pitch/yaw directions and/or opening/closing motions of an adjustment handle.

Another object of the present invention is to provide a tool for minimally invasive surgery, which a user can freely actuate without the help of a special drive element.

A further object of the present invention is to provide a tool for minimally invasive surgery, which features small volume, lightweight, and convenient movability.

In accordance with an aspect of the present invention, there is provided a tool for minimally invasive surgery comprising, an elongated shaft having a predetermined length, an adjustment handle manually controllable by a user, a pitch direction handling part and a yaw direction handling part positioned around one end of the elongated shaft for transferring motions in pitch and yaw directions following the actuation of the adjustment handle, a pitch direction actuating part and a yaw direction actuating part positioned around the other end of the elongated shaft for operating corresponding to the operations from the pitch direction handling part and the yaw direction handling part, respectively, an end effector controllable by the pitch direction actuating part and the yaw direction actuating part, and a plurality of cables for transferring the from the pitch direction handling part and the yaw direction handling part to the pitch direction actuating part and the yaw direction actuating part, respectively.

BRIEF DESCRIPTION OF THE DRAWINGS

The above and other objects and features of the present invention will become apparent from the following description of the preferred embodiments given in conjunction with the accompanying drawings, in which.

DETAILED DESCRIPTION OF THE PREFERRED EMBODIMENT

In the following detailed description, reference is made to the accompanying drawings that show, by way of illustration, specific embodiments in which the invention may be practiced. These embodiments are described in sufficient detail to enable those skilled in the art to practice the invention. It is to be understood that the various embodiments of the invention, although different, are not necessarily mutually exclusive. The following detailed description is, therefore, not to be taken in a limiting sense, and the scope of the present invention is defined only by the appended claims that should be appropriately interpreted along with the full range of equivalents to which the claims are entitled.

Hereinafter, preferred embodiments of the present invention will be explained in detail with reference to the accompanying drawing.

Figure 1:
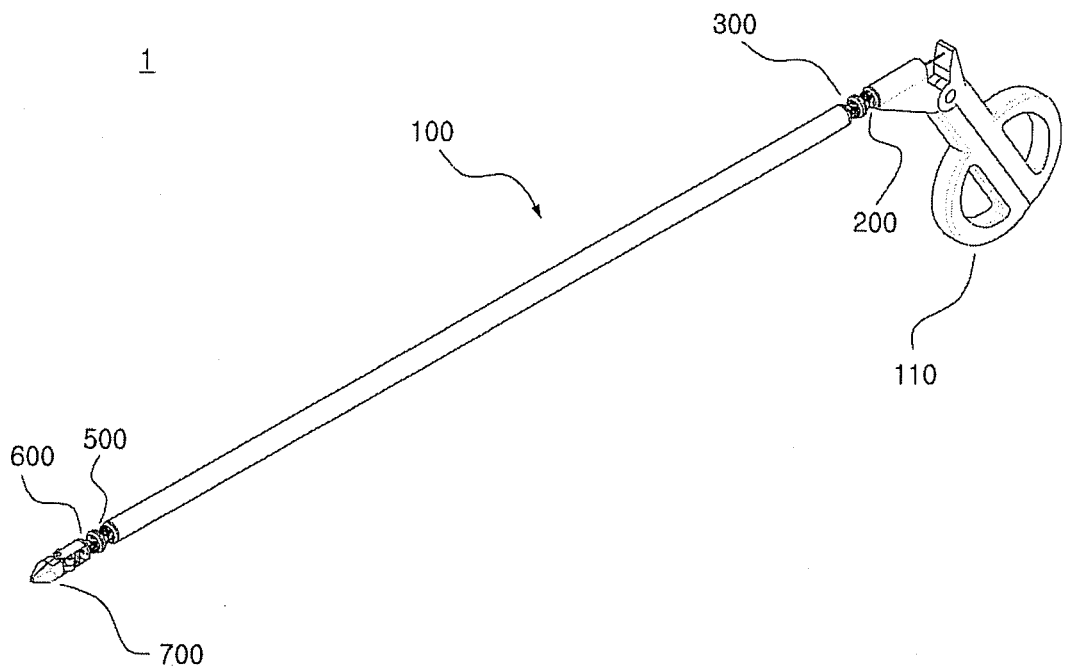
FIG. 1 is a perspective view showing the outer appearance of a tool for minimally invasive surgery, in accordance with one embodiment of the present invention.

FIG. 1 is a perspective view showing the outer appearance of a tool 1 for minimally invasive surgery, in accordance with one embodiment of the present invention. Referring to FIG. 1, the tool 1 for minimally invasive surgery includes an elongated shaft 100 of a predetermined length, which has one or plural spaces inside (e.g., pipe-shape, lotus-shaped, or spiral-shaped space), pitch and yaw direction handling parts 200 and 300 positioned around one end of the elongated shaft 100, and yaw and pitch direction actuating parts 500 and 600 positioned around the other end of the elongated shaft 100. In addition, the tool 1 for minimally invasive surgery in accordance with one embodiment of the present invention further includes an adjustment handle 110 and an end effector 700 that are connected to both ends of the elongated shaft 100, respectively.

Figure 2:
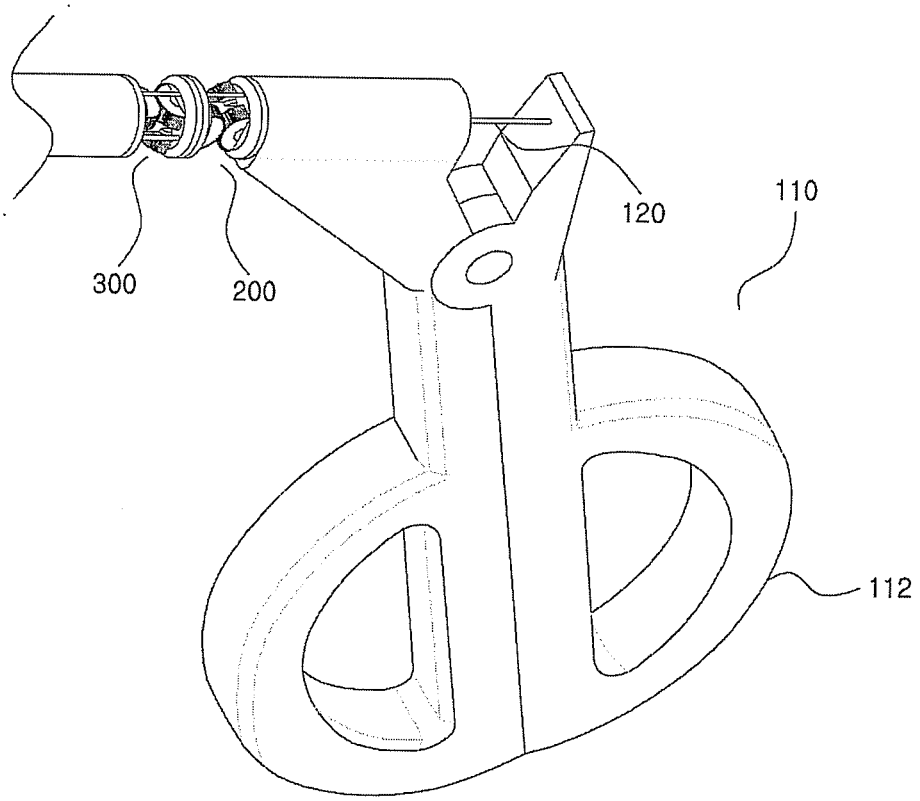
FIGS. 2 and 3 each show a side view and a plan view of an adjustment handle, and pitch/yaw direction handling parts connected thereto, in accordance with one embodiment of the present invention.
Figure 3:
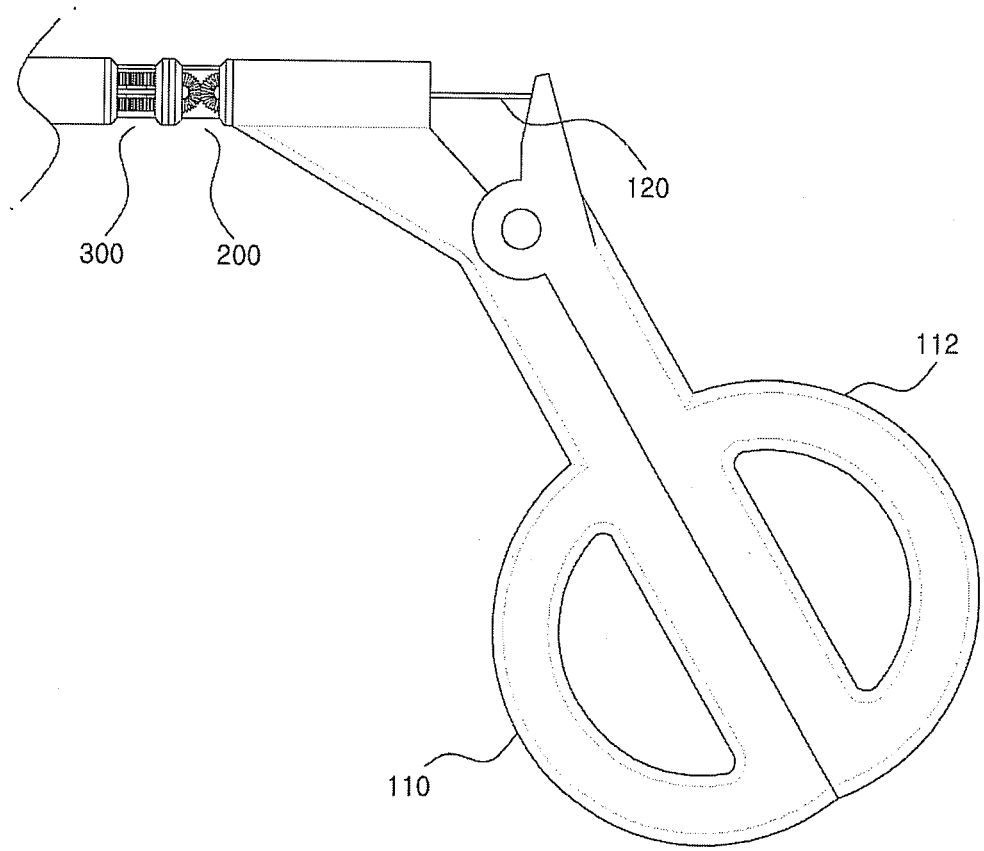

FIGS. 2 and 3 each show a perspective view and a plan view of the adjustment handle 110, and pitch/yaw direction handling parts 200 and 300 connected thereto. Referring to FIGS. 2 and 3, the adjustment handle 100 is configured in such a manner that an enclosure 112 can pull out or release an opening/closing cable 120 while rotating along the rotation axis of the adjustment handle 110 (note that the opening/closing cable 120 is not always necessary depending on the kind of the end effector 700 used). More specifically, for the adjustment handle 110, two rods a user can grasp are connected to each other by the rotation axis, and two enclosures 112 of a semi-circular shape are formed symmetrically to each other on ends of the rods that are connected by the rotation axis. As one of the enclosures is opened or closed, the opening/closing cable 120 is either pulled out or released. Meanwhile, the pitch direction handling part 200 and the yaw direction handling part 300 are configured to operate following the actuation of the adjustment handle 110 in pitch and yaw directions.

Figure 4:
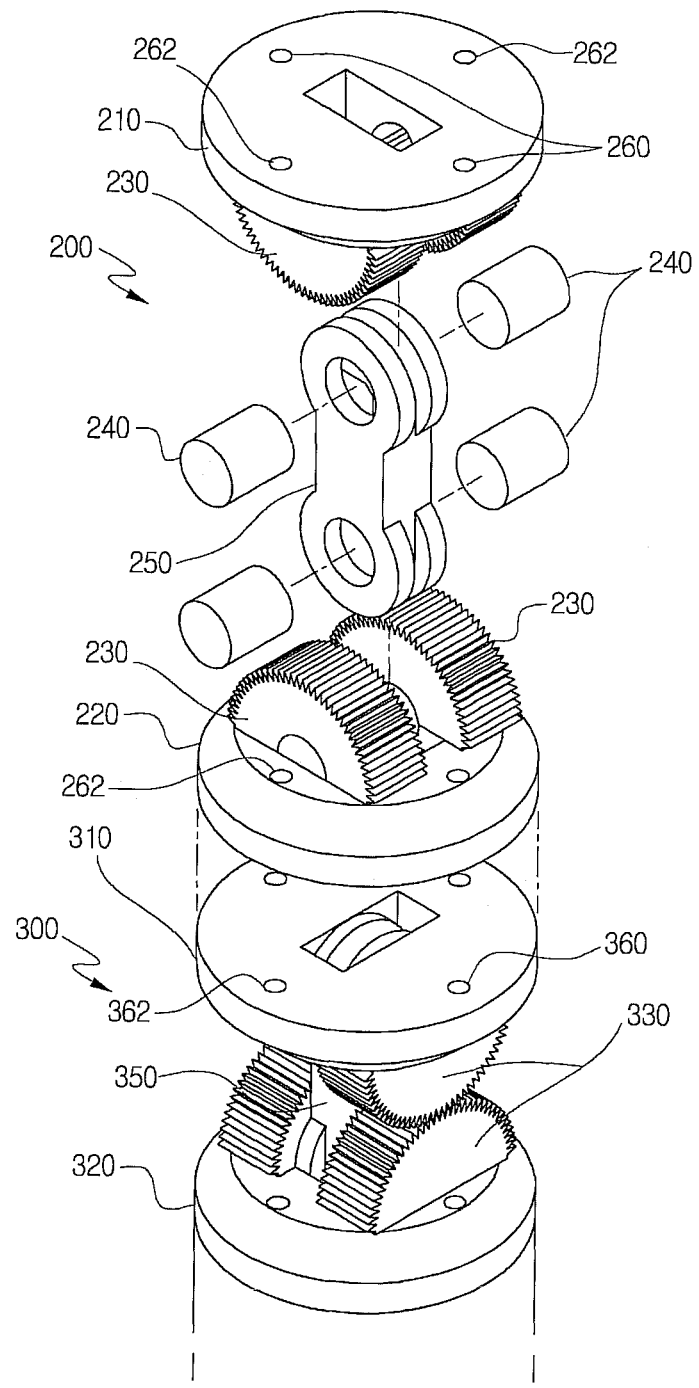
FIG. 4 is an exploded perspective view of a pitch direction handling part and a yaw direction handling part, in accordance with one embodiment of the present invention.

FIG. 4 is an exploded perspective view describing the configuration of the pitch direction handling part 200 and the yaw direction handling part 300, in accordance with one embodiment of the present invention. It shows a detailed configuration of the pitch direction handling part 200 to which a motion of the adjustment handle 110 in the pitch direction is transferred, and the yaw direction handling part 300 to which a motion of the adjustment handle 110 in the yaw direction is transferred. At this time, plane of the pitch direction handling part 200 and plane of the yaw direction handling part 300 cross each other at right angles.

First, the configuration of the pitch direction handling part 200 will be explained.

First and second circular plates 210 and 220 are spaced apart from each other by a predetermined distance, and two pairs of pitch direction adjustment gears 230 in semi-circular shape and same size are disposed on the plane that lies at right angles to the planes of the first and the second plates 210 and 220, parallel to each other with respect to the center axis of the first and the second plates 210 and 220. In FIG. 4, although the first and the second plates 210 and 220 where the pitch direction adjustment gears 230 are disposed are in circular form occupying a minimal area, they do not need to be circular all the time but may be in any other forms.

Figure 5:
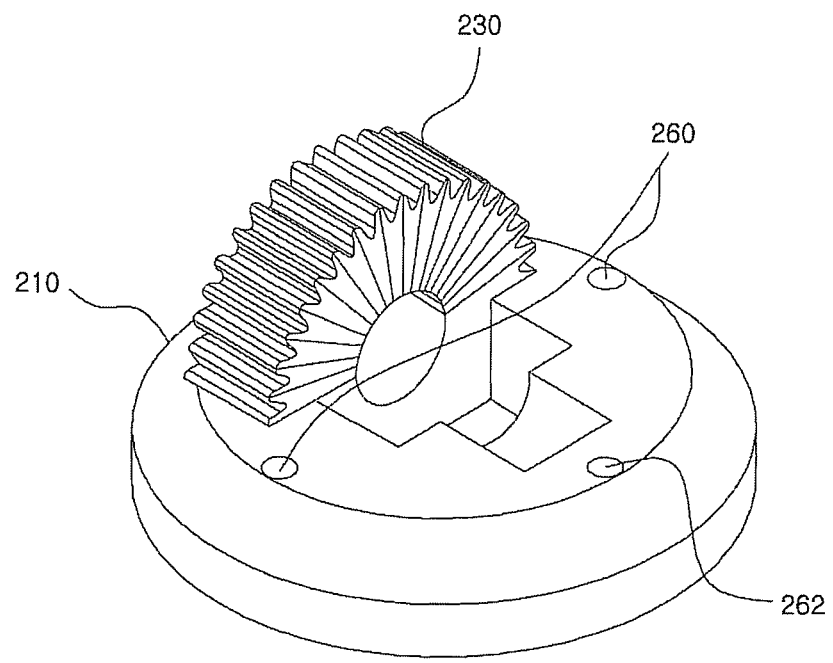
FIG. 5 shows a state in which a pitch direction adjustment gear is disposed onto a first plate of the pitch direction handling part, in accordance with one embodiment of the present invention.
Figure 6:
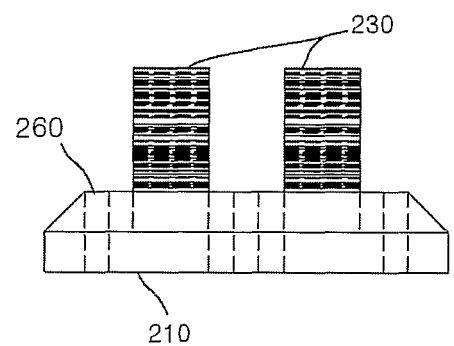
FIGS. 6 and 7 each show a state in which two pitch direction adjustment gears are disposed parallel to each other in pair at a predetermined distance, in accordance with one embodiment of the present invention.
Figure 7:
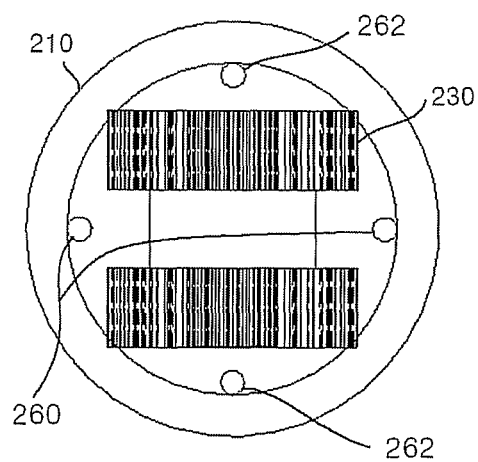

The following is an explanation about different layouts of pitch direction adjustment gear(s) shown in FIGS. 5, 6, and 7. FIG. 5 shows a state where a pitch direction adjustment gear 230 is disposed onto a first plate 210, in accordance with one embodiment of the present invention. In FIG. 5, even though there seems to be only one pitch direction adjustment gear 230 disposed on the plate, the other pitch direction adjustment gear 230 is just hidden from view, to clarify the status of the installation of those pitch direction adjustment gears 230. That is, there are actually two pitch direction adjustment gears 230 in pair, which is preferably disposed onto the first plate 210.

FIGS. 6 and 7 each show a state in which two pitch direction adjustment gears 230 are disposed parallel to each other in pair at a predetermined distance, in accordance with one embodiment of the present invention. In accordance with one embodiment of the present invention, the operation of the pitch direction handling part 200 is still controllable following the actuation of the adjustment handle 110 with only one pitch direction adjustment gear 230 deposited on one plate, but at least two or more pitch direction adjustment gears 230 should be provided to maintain operational stability. Meanwhile, each pair of the pitch direction adjustment gears 230 disposed onto the first plate 210 and the second plate 220 preferably maintains the same distance between the gears, and the pitch direction adjustment gears 230 disposed onto the first plate 210 and the pitch direction adjustment gears 230 disposed onto the second plate 220 are formed with the same pitch to intermesh.

Returning back to FIG. 4, there is a circular space at the center between the pitch direction adjustment gear 230 pairs disposed onto the first and the second plates 210 and 220, and cylindrical joint rotation axes 240 are rotatably inserted in the space. At this time, it is preferable that the central axis of the pitch direction adjustment gears 230 coincides with the central axis of the joint rotation axis 240. Meanwhile, the length of the inserted joint rotation axes 240 is determined in a manner that it is longer than the thickness of each of the pitch direction adjustment gears 230 but not too long to make ends of the joint rotation axes that are arranged in parallel come in contact with each other. Moreover, since the pitch direction adjustment gears 230 are formed in semi-circular shape, the center of each of the pitch direction adjustment gears 230 is located on the surface of the first and the second plates 210 and 220 accordingly.

Meanwhile, referring to FIG. 4, the semi-circular shape of the pitch direction adjustment gear 230 is for limiting the operation range of the adjustment handle 110 in the pitch direction to 180 degrees. This implies that the pitch direction adjustment gears 230 may take another form, e.g., a sector shape, instead of the semi-circular shape, to set the operation range differently.

To make the pitch direction adjustment gears 230 on the first and the second plates 210 and 220 engaged with each other or intermeshed, a first pitch link 250 is placed between the first and the second plates 210 and 220. More details on this will now be explained with reference to FIGS. 8, 9, and 10.

Figure 8:
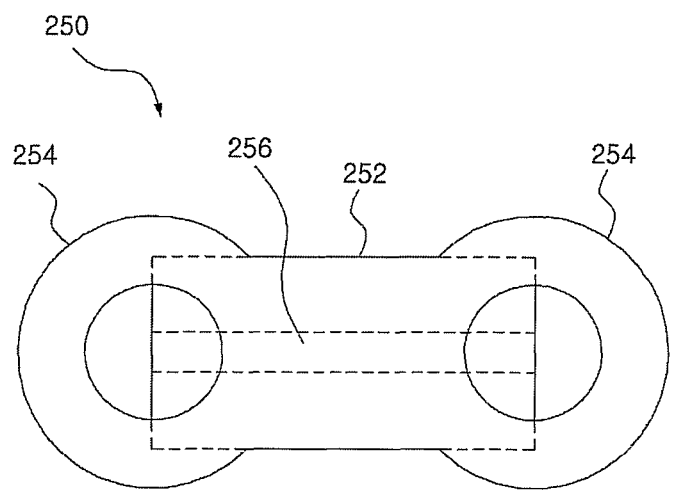
FIGS. 8, 9, and 10 each show a front view, a side view, and a perspective view of the configuration of a first pitch link, in accordance with one embodiment of the present invention.
Figure 9:
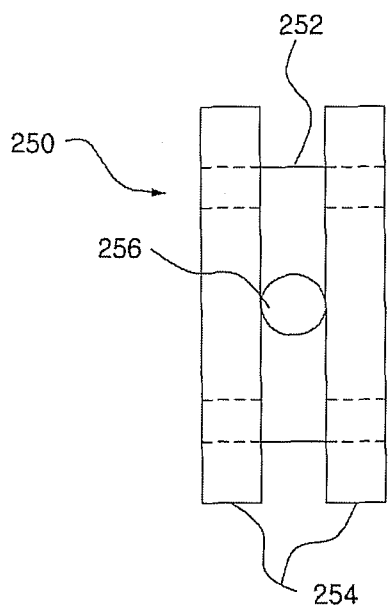
Figure 10:
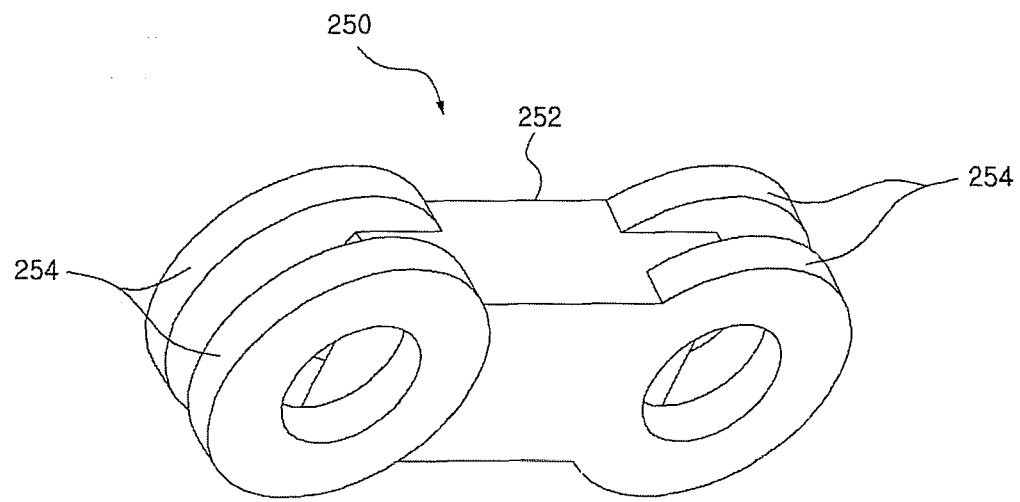

FIGS. 8, 9, and 10 each show a front view, a side view, and a perspective view of the configuration of the first pitch link 250, in accordance with one embodiment of the present invention. As shown, the first pitch link 250 includes a body 252 in a substantially cuboid shape of predetermined length, and two pairs of rotation rings 254, each pair being formed at either end of the body with a predetermined distance between them.

In fact, one end of the joint rotation axis 240 that has been inserted in the center of the pitch direction adjustment gears 230 is inserted in the rotation ring 254 of the first pitch link 250, so as to enable the pitch direction adjustment gear 230 to rotate. In this way, the pitch direction adjustment gears 230 on the first and the second plates 210 and 220 rotate in intermeshed state, and such rotation takes place about the joint rotation axes 240 that are inserted in the rotation rings 254 on both ends of the first pitch link 250.

Meanwhile, as depicted in FIG. 9, the body 252 of the first pitch link 250 has a through hole 256 formed along the central axis of its length direction, through which the opening/closing cable 120 that connects the adjustment handle 110 and the end effector 700 passes. Preferably, the through hole 256 is positioned at the center of the body 252.

For information, a second pitch link 650 and first and second yaw links 350 and 550 (to be described later) are also formed in the same manner as the first pitch link 250.

Referring back to FIGS. 4, 5, 6, and 7, there are four through holes 260 and 262 formed in each of the first and the second plates 210 and 220. Preferably, those four through holes 260 and 262 are formed at angular distances of 90 degrees about the center of the first and the second plates 210 and 220, two 260 of which are pitch cable insert holes and the other two 262 of which are yaw cable insert holes.

After the pitch direction handling part 200 is configured as discussed above, a first plate 310 of the yaw direction handling part 300 is closely adhered to the rear side of the second plate 220 of the pitch direction handling part 200.

Similar to the pitch direction handling part 200, the yaw direction handling part 300 is constituted by first and second plates 310 and 320 spaced apart from and opposite to each other at a predetermined distance, each plate having a pair of yaw direction adjustment gears 330. Two pairs of the yaw direction adjustment gears 330 disposed onto the first and the second plates 310 and 320 are intermeshed and they stay in intermeshed state with the help of a first yaw link 350.

The yaw direction handling part 300 is configured substantially in the same manner as the pitch direction handling part 200 except that the internal constituents of the yaw direction handling part 300 operate in a direction orthogonal to that of the internal constituents of the pitch direction handling part 200, so further details on the configuration will be omitted here.

However, it should be noted that, when adhering the first plate 310 of the yaw direction handling part 300 to the rear side of the second plate 220 of the pitch direction handling part 200 that the through holes formed in the second plate 220 of the pitch direction handling part 200 should be aligned with or coincide with the through holes formed in the first plate 310 of the yaw direction handling part 300.

Figure 11:
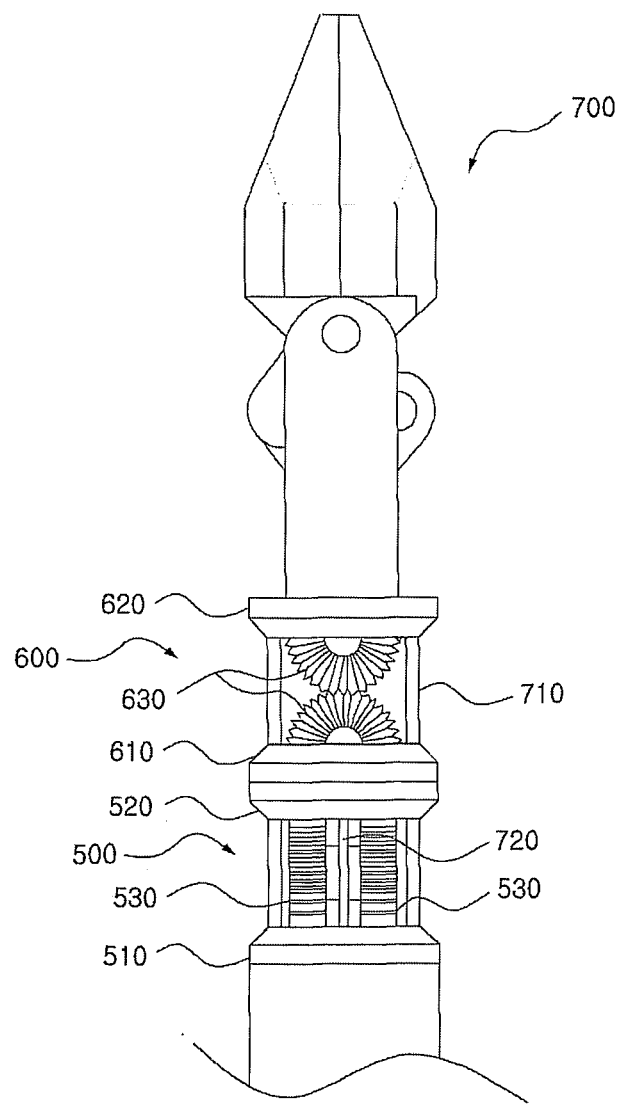
FIGS. 11, 12, and 13 each show a front view, a perspective view, and a side view of a pitch direction actuating part, a yaw direction actuating part, and an end effector, in accordance with one embodiment of the present invention.
Figure 12:
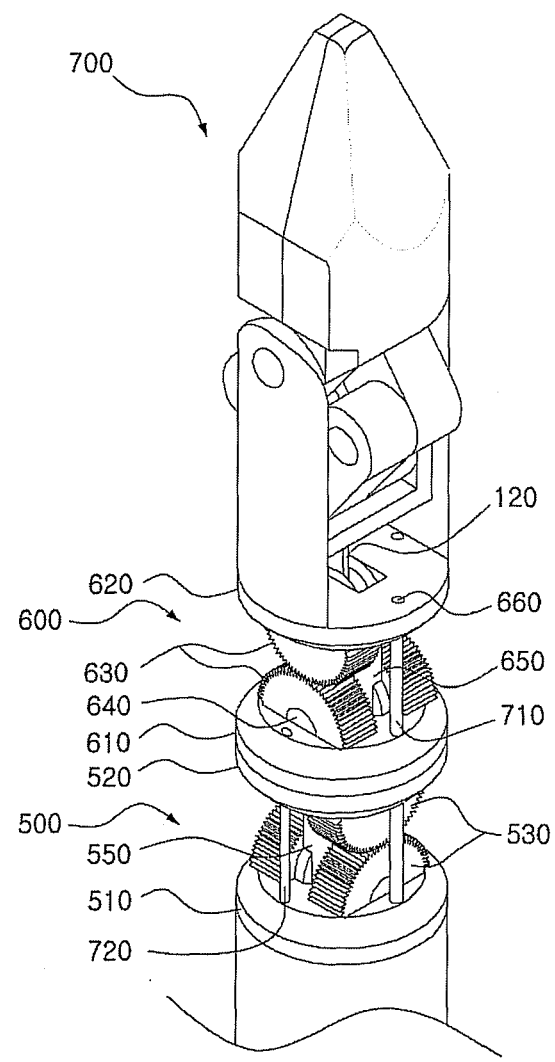
Figure 13:
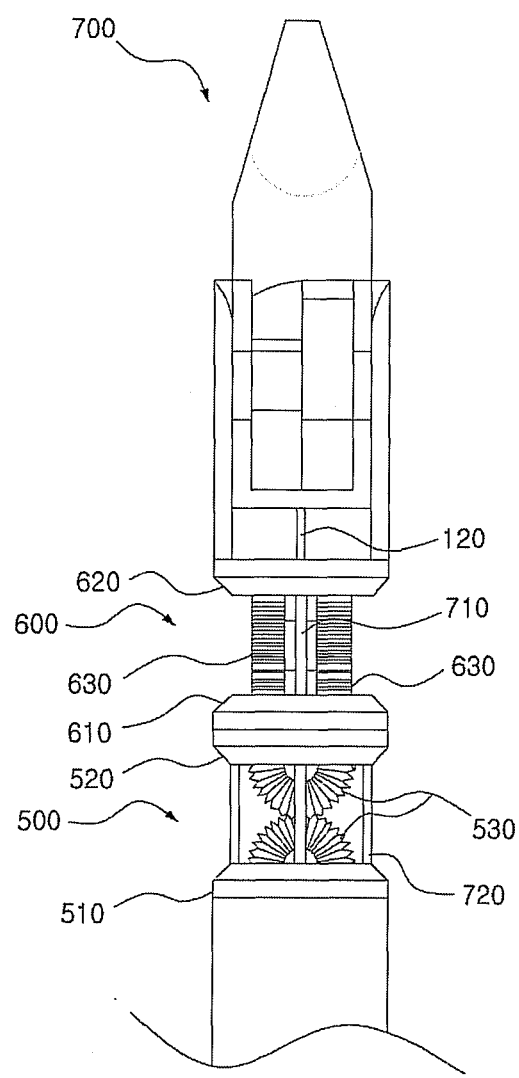

Next, a description on the yaw/pitch direction actuating parts 500 and 600 and the end effector 700 will be provided with reference to FIGS. 11, 12, and 13. FIGS. 11, 12, and 13 each show a front view, a perspective view, and a side view of the elements mentioned above.

Referring first to FIG. 11, the yaw direction actuating part 500 includes a third plate 510 and a fourth plate 520 disposed to face each other, each plate having a pair of yaw direction adjustment gears 530. As in the yaw direction actuating part 300, two pairs of the yaw direction adjustment gears 530 disposed onto the third and the fourth plates 510 and 520 are intermeshed and they stay in intermeshed state with the help of a second yaw link 550, so further details on this will not be provided hereinafter.

In addition, the pitch direction actuating part 600 includes a third plate 610 and a fourth plate 620 arranged to face each other, each plate having a pair of pitch direction adjustment gears 630. As in the pitch direction actuating part 200, two pairs of the pitch direction adjustment gears 630 disposed onto the third and the fourth plates 610 and 620 are intermeshed and they stay in intermeshed state with the help of a second pitch link 650, so further details on this will not be provided hereinafter.

Meanwhile, the yaw direction actuating part 500 and the pitch direction actuating part 600 are configured to operate in directions orthogonal to each other.

The end effector 700 connected to one end of the pitch direction actuating part 600 operates corresponding to the opening/closing operation of the adjustment handle 110, and is used as a tool for the surgery inside the body, such as, a clamp, a grasper, scissors, a stapler, tweezers, etc. If necessary, unlike the one shown in the drawing, the end effector 700 in accordance with one embodiment of the present invention may be a hook-shaped electrode which does not need to be opened or closed.

The pitch direction handling part 200 with the above-described configuration is connected to the pitch direction actuating part 600 through a pitch cable 710, and the yaw direction handling part 300 is connected to the yaw direction actuating part 500 through a yaw cable 720. Thus, when a user manually controls the adjustment handle 110 in a pitch/yaw direction, the handling on the part of the user in the pitch/yaw direction handling parts 200 and 300 is transferred to the pitch/yaw direction actuating parts 600 and 500 through the pitch cable 710 and the yaw cable 720 (i.e., the motions in the pitch and yaw directions are substantially independent of each other). At this time, the pitch cable 710 and the yaw cable 720 are arranged passing through the inside of the shaft 100. To prevent entanglement of cables inside the shaft 100 or to switch (invert) the direction of cables, a guider may be installed additionally.

An example of how the pitch cable 710 and the yaw cable 720 are connected will now be explained.

As noted earlier, the pitch cable insert holes 260 and the yaw cable insert holes 262 are formed in the first plate 210 of the pitch direction handling part 200. Here, one of the pitch cable insert holes 260 formed in the first plate 210 of the pitch direction handling part 200 is for connectively receiving one end of pitch cable 710, and one of the pitch cable insert holes 660 formed in the fourth plate 620 of the pitch direction actuating part 600 is for connectively receiving the other end of the pitch cable 710. Although it is illustrated here and below that the cables are secured in the through holes, it should be noted that, as long as the cables operate according to the technical aspect of the present invention, they do not necessarily need to be secured in the through holes but may be secured to other fixed elements (e.g., the plates) near the through holes.

In similar manner, the pitch cable 710 is connectively secured in another pitch cable insert hole 260 formed in the first plate 210 and in another pitch cable insert hole 660 formed in the fourth plate 620, such that the pitch direction handling part 200 and the pitch direction actuating part 600 can be connected by a pair of pitch cables 710. Here, it is preferable that the pitch cables 710 used for connecting the pitch direction handling part 200 and the pitch direction actuating part 600 are connected parallel to each other and have the same elasticity. Alternatively, the pitch cables 710 may take the form of $\mathbb{X}$ in the presence of the guider and the plates as noted before.

Also, the pitch cables 710 are connected passing through the inside of the shaft 100 between the pitch direction handling part 200 and the pitch direction actuating part 600.

Now, an explanation about the yaw cables 720 will be given.

Two yaw cable insert holes 362 formed in the yaw direction handling part 300 are for connectively receiving one end of each of the yaw cables 720, respectively, and the yaw cable insert holes formed in the fourth plate 520 of the yaw direction actuating part 500 are for connectively receiving the other end of each of the yaw cables 720.

Again, the yaw cables 720 used for connecting the yaw direction handling part 300 and the yaw direction actuating part 500 are connected parallel to each other and have the same elasticity (of course, the yaw cables 720 may be in form of $\mathbb{X}$ as well). Connection of such yaw cables 720 is similar to that of the pitch cables 710 explained earlier.

The operation of the tool 1 for minimally invasive surgery as configured above in accordance with one embodiment of the present invention will now be explained.

First, the tool 1 for minimally invasive surgery is disposed in such a manner that the centers of the pitch/yaw direction handling parts 200 and 300, the shaft 100, and the yaw/pitch direction actuating parts 500 and 600 are aligned to coincide with each other, as shown in FIG. 1.

A surgeon who performs the minimally invasive surgery puts his or her hand in the enclosure 112 of the adjustment handle 110 that is installed at one end of the tool 1 for minimally invasive surgery and holds the adjustment handle 110.

Hereinafter, it is assumed that (+) and (−) motions in the yaw direction designate motions in the right and left sides about the surgeon for convenience of explanation about the operation of the adjustment handle 110 in the yaw direction. Similarly, it is assumed that (+) and (−) motions in the pitch direction designate motions in the upper and lower sides about the surgeon for convenience of explanation about the operation of the adjustment handle 110 in the pitch direction.

Figure 14:
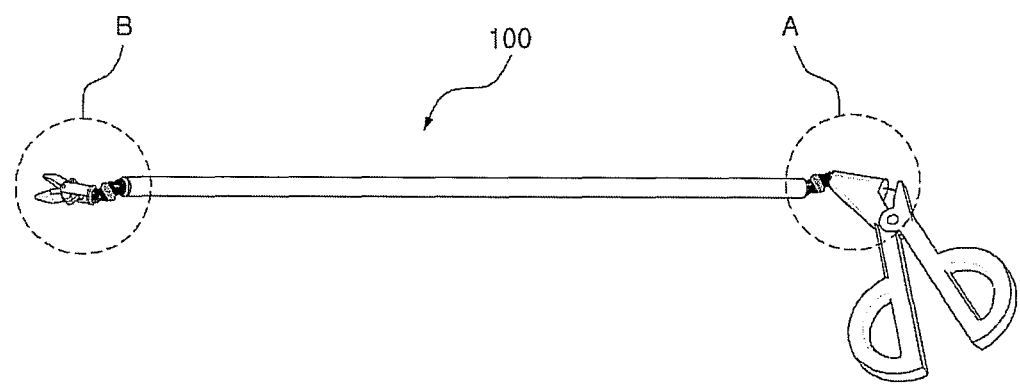
FIGS. 14, 15, and 16 each show different usage examples of a tool for minimally invasive surgery in accordance with the present invention.
Figure 15:
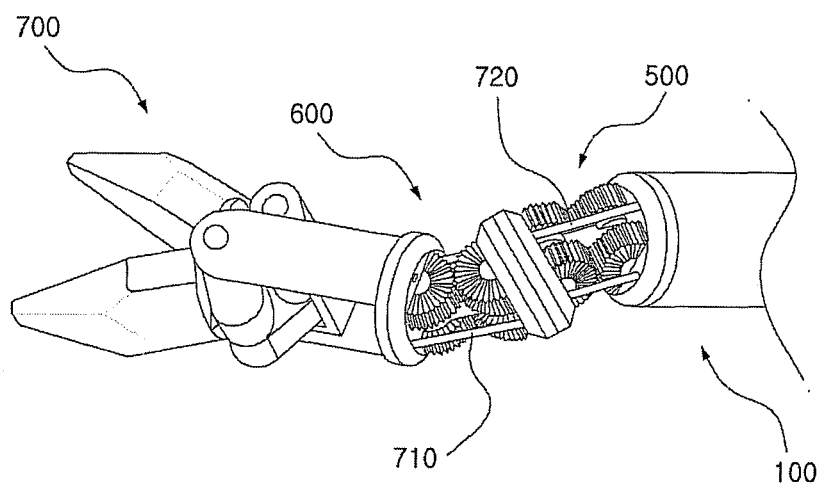
Figure 16:
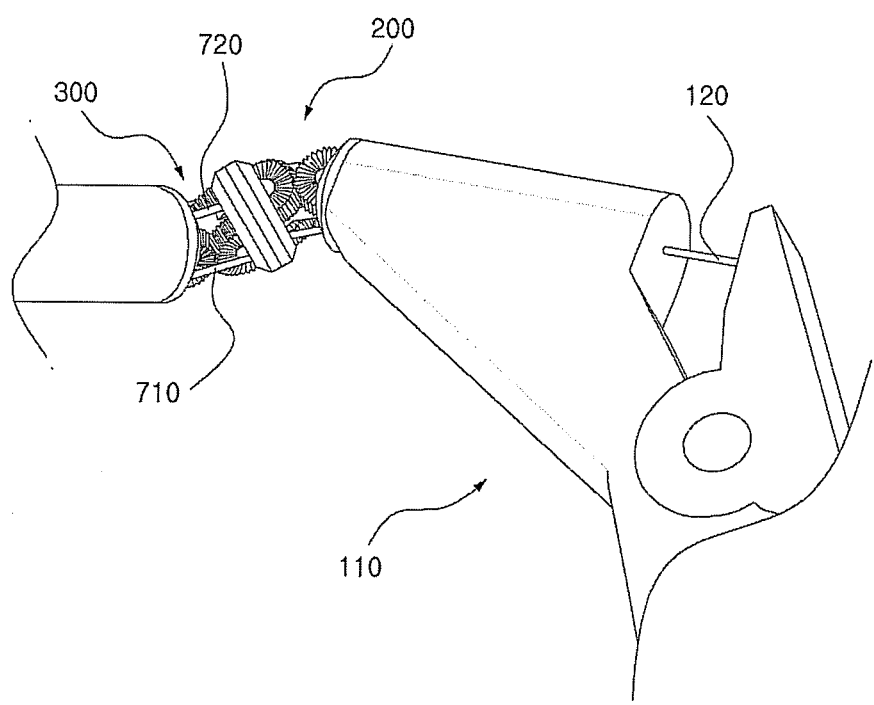

FIG. 14 illustrates a usage example of the tool 1 for minimally invasive surgery in accordance with the present invention, FIG. 15 is a detailed view of 'B' portion in FIG. 14, and FIG. 16 is a detailed view of 'A' portion in FIG. 14.

When the surgeon holding the adjustment handle 110 rotates the adjustment handle 110 downwardly, the upper side cable out of the pitch cables 710 having one end connectively secured in the pitch cable insert holes 260 that are formed in the first plate 210 of the pitch direction handling part 200 is pulled towards the body of the surgeon, so that the lower side cable out of the pitch cables 710 is released in opposite direction, thereby making the end effector 700 rotate upwardly as shown in FIG. 14. Needless to say, when the surgeon rotates the adjustment handle 110 in opposite direction, the end effector 700 will rotate in opposite direction as well.

Meanwhile, when the surgeon holding the adjustment handle 110 rotates the adjustment handle 110 to the left, the right side cable out of the yaw cables 720 having one end connectively secured in the yaw cable insert holes 362 that are formed in the first plate 310 of the yaw direction handling part 300 is pulled towards the body of the surgeon, so that the left side cable out of the yaw cables 720 is released in opposite direction, thereby making the end effector 700 rotate to the right as shown in the drawing. Needless to say, when the surgeon rotates the adjustment handle 110 in opposite direction, the end effector 700 will rotate in opposite direction as well.

While this embodiment introduced that the end effector 700 should operate in opposite direction to the direction where the surgeon manually rotates the adjustment handle 110, cables may be installed, if needed, so that the adjustment handle 110 and the end effector 700 operate in the same direction.

If all of the adjustment gears used for the handling parts and the actuating parts are of the same size, the displacement amount of the adjustment handle 110 and the displacement amount of the end effector 700 are at the ratio of 1:1. This ratio can be varied by using different sized adjustment gears.

For instance, if the gear ratio is not 1, that is, if the pitch direction adjustment gears 230 of the pitch direction handling part 200 have a larger radius than the pitch direction adjustment gears 630 of the pitch direction actuating part 600, the gear ratio becomes above 1. At this time, since the pitch direction adjustment gears 630 rotate at a greater angle than that of the manual control by the surgeon, the end effector 700 eventually rotates further than the adjustment handle 110. Of course, if the gear ratio is below 1, the displacement amount of the end effector 700 is smaller than the manually controlled angle of the adjustment handle 110.

Meanwhile, if the surgeon closes the adjustment handle 110 while leaving the end effector 700 in a state where it faces a desired direction with the control over the adjustment handle 110, the closing motion of the adjustment handle 110 is transferred to the end effector 700 via the opening/closing cable 120, thereby causing the end effector 700 to close. On the contrary, if the surgeon opens the adjustment handle 110, the end effector 700 will return to its original open state with the help of the resilient force from restoration springs (not shown) installed therein. If needed, the surgeon may use the end effector 700 with an opening/closing function for surgery. While this embodiment has assumed that the end effector 700 is opened following the opening of the adjustment handle 110 by the surgeon, it is also possible to configure in such a way that they operate in an opposite manner depending on the kind of the end effector 700 used. Also, as discussed earlier, it is to be understood that the opening/closing cable 120 may be pulled either by the upper side enclosure 112 or by the lower side enclosure 112 out of the two enclosures 112 of the adjustment handle 110.

Figure 17:
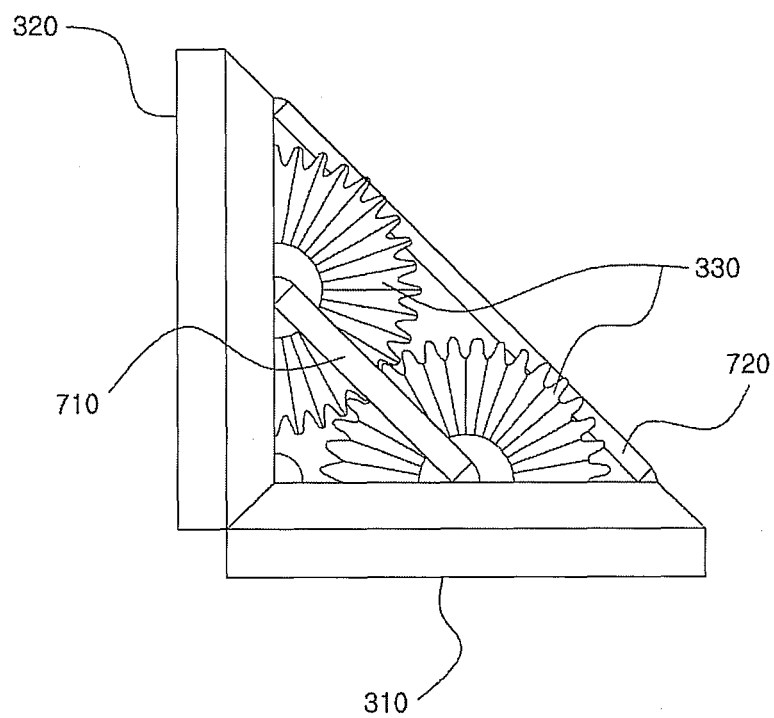
FIG. 17 shows a detailed configuration of a yaw direction handling part, in accordance with one embodiment of the present invention.

Finally, FIG. 17 is a detailed view of the configuration of the yaw direction handling part 300, in accordance with one embodiment of the present invention. As shown in FIG. 17, the first and the second plates 310 and 320 that are parallel to each other may be turned around by external manipulation to be at right angles (90 degrees) to each other within the yaw direction handling part 300. Also as shown in FIG. 17, when the first and the second plates 310 and 320 are at right angles (90 degrees) to each other, the pitch cables 710 do not almost change in terms of length, unlike the yaw cables 720 in the yaw direction handling part 300. Thus, the pitch direction handling part 200 and the yaw direction handling part 300 can operate substantially independent of each other. Optionally, facing edges of the first and the second plates 310 and 320 may undergo edge grinding at about 45 degrees to prevent the edges of the plates from being damaged by collision with each other.

As discussed earlier, the tool for minimally invasive surgery in accordance with the present invention is provided with an end effector which features high-degree-of-freedom motion corresponding to the user's manual control over an adjustment handle.

In addition, the tool for minimally invasive surgery in accordance with the present invention is configured for any user to operate with easiness.

Moreover, the tool for minimally invasive surgery in accordance with the present invention can be manufactured and supplied at low costs, and has small volume and lightweight, making easier to supply.

While the present invention has been described with respect to certain preferred embodiments, it will be apparent to those skilled in the art that various changes and modifications may be made without departing from the scope of the invention as defined in the following claims.

What is claimed is:

1. Tool for minimally invasive surgery comprising,
  an elongated shaft having a predetermined length,
  an adjustment handle manually controllable by a user's actuation thereof,
  a pitch direction handling part and a yaw direction handling part positioned around one end of the elongated shaft for transferring motions in pitch and yaw directions following the actuation of the adjustment handle,
  a pitch direction actuating part and a yaw direction actuating part positioned around the other end of the elongated shaft for operating corresponding to the operations from the pitch direction handling part and the yaw direction handling part, respectively,
  an end effector controllable by the pitch direction actuating part and the yaw direction actuating part, and
  a plurality of cables for transferring the motions from the pitch direction handling part and the yaw direction handling part to the pitch direction actuating part and the yaw direction actuating part, respectively, wherein the adjustment handle, the pitch direction handling part, the yaw direction handling part, the pitch direction actuating part and the yaw direction actuating part are disposed in a series along the elongated shaft, and
  wherein the pitch direction handling part comprises,
  a first plate and a second plate of the pitch direction handling part, the first plate and the second plate are spaced apart from each other and are disposed substantially parallel to each other,
  at least two adjustment gears disposed onto the first plate and at least two adjustment gears disposed onto the second plate of the pitch direction handling part,
  a link disposed between the first and second plate of the pitch direction handling part for enabling the two adjustment gears to intermesh, and
  a joint rotation axis inserted in a middle point between the at least two adjustment gears, and
  wherein the yaw direction handling part comprises,
  a first plate and a second plate of the yaw direction handling part, the first plate and the second plate are spaced apart from each other and are disposed substantially parallel to each other,
  at least two adjustment gears disposed onto the first plate and at least two adjustment gears disposed onto the second plate of the yaw direction handling part, and
  a joint rotation axis inserted in a middle point between the at least two adjustment gears, and
  wherein the second plate of the pitch direction handling part and the first plate of the yaw direction handling part are adjacent to each other, and the adjustment handle is physically connected to the pitch direction handling part through the first plate of the pitch direction handling part.

2. The tool as claimed in claim 1, wherein at least one space is formed inside the elongated shaft.

3. The tool as claimed in claim 2, wherein the plurality of cables are formed in the space of the elongated shaft.

4. The tool as claimed in claim 1, further comprising,
  an opening and closing cable for transferring the opening and closing operation of the adjustment handle to the end effector.

5. The tool as claimed in claim 1, wherein the yaw direction handling part further comprises,
  a link disposed between the first and second plate of the yaw direction handling part for enabling the at least two adjustment gears to intermesh.

6. The tool as claimed in claim 1, wherein the first plate and the second plate of the pitch direction handling part have a plurality of cable insert holes formed therethrough.

7. The tool as claimed in claim 1, wherein the link comprises,
  a body in a substantially cuboid shape, and
  at least two rotation rings, each being formed at either end of the body and configured to enable the joint rotation axis to rotate.

8. The tool as claimed in claim 7, wherein the body has a through hole formed along its central axis of a length direction.

9. The tool as claimed in claim 1, wherein the pitch direction actuating part comprises,
  a pair of plates spaced apart from each other and disposed substantially parallel to each other,
  at least two adjustment gears disposed onto the pair of plates,
  a joint rotation axis inserted in a middle point between the at least two adjustment gears, and a link for enabling the at least two adjustment gears to intermesh.

10. The tool as claimed in claim 1, wherein the yaw direction actuating part comprises,
a pair of plates spaced apart from each other and disposed substantially parallel to each other,
at least two adjustment gears disposed onto the pair of plates,
a joint rotation axis inserted in middle point between the at least two adjustment gears, and
a link for enabling the at least two adjustment gears to intermesh.

11. The tool as claimed in claim 9, wherein the pair of plates has a plurality of cable insert holes formed therethrough.

12. The tool as claimed in claim 9, wherein the link comprises,
a body in a substantially cuboid shape, and
at least two rotation rings, each being formed at either end of the body and configured to enable the joint rotation axis to rotate.

13. The tool as claimed in claim 12, wherein the body has a through hole formed along its central axis of a length direction.

14. The tool as claimed in claim 1, wherein the plurality of cables comprise,
a pitch cable for transferring the operation from the pitch direction handling part to the pitch direction actuating part, and
a yaw cable for transferring the operation from the yaw direction handling part to the yaw direction actuating part.

15. The tool as claimed in claim 14, wherein the pitch cable is connected and fixed to cable insert holes formed on either of the pitch direction handling part and the pitch direction actuating part.

16. The tool as claimed in claim 14, wherein the yaw cable is connected and fixed to cable insert holes formed on either of the yaw direction handling part and the yaw direction actuating part.

17. The tool as claimed in claim 5, wherein the first plate and the second plate of the yaw direction handling part have a plurality of cable insert holes formed therethrough.

18. The tool as claimed in claim 5, wherein the link comprises,
a body in a substantially cuboid shape, and
at least two rotation rings, each being formed at either end of the body and configured to enable the joint rotation axis to rotate.

19. The tool as claimed in claim 10, wherein the pair of plates has a plurality of cable insert holes formed therethrough.

20. The tool as claimed in claim 10, wherein the link comprises,
a body in a substantially cuboid shape, and
at least two rotation rings, each being formed at either end of the body and configured to enable the joint rotation axis to rotate.

* * * * *